(12) United States Patent
Nishtala

(10) Patent No.: US 8,715,254 B2
(45) Date of Patent: May 6, 2014

(54) RENAL MONITOR

(75) Inventor: Vasu Nishtala, Snellville, GA (US)

(73) Assignee: C. R. Bard, Inc., Murray Hill, NJ (US)

(*) Notice: Subject to any disclaimer, the term of this patent is extended or adjusted under 35 U.S.C. 154(b) by 429 days.

(21) Appl. No.: 12/527,977

(22) PCT Filed: Feb. 18, 2008

(86) PCT No.: PCT/US2008/054207
§ 371 (c)(1),
(2), (4) Date: Aug. 20, 2009

(87) PCT Pub. No.: WO2008/103627
PCT Pub. Date: Aug. 28, 2008

(65) Prior Publication Data
US 2010/0121220 A1    May 13, 2010

Related U.S. Application Data

(60) Provisional application No. 60/890,851, filed on Feb. 21, 2007.

(51) Int. Cl.
*A61M 1/00* (2006.01)
(52) U.S. Cl.
USPC .......................................................... 604/318
(58) Field of Classification Search
USPC ........................ 600/573, 581, 584; 604/318
See application file for complete search history.

(56) References Cited

U.S. PATENT DOCUMENTS 4,343,316 A   8/1982 Jespersen
5,476,434 A * 12/1995 Kalb et al. .................. 600/30
5,704,353 A   1/1998 Kalb et al.
6,379,969 B1 * 4/2002 Mauze et al. ............... 436/68
2003/0019115 A1 * 1/2003 Tannenbaum ............... 33/1 SB (Continued)

FOREIGN PATENT DOCUMENTS

JP       57017656 A    1/1982
JP     H11502630 A    3/1999

(Continued)

OTHER PUBLICATIONS

Erlenkotter et al., Biosensors and Flow-through System for the Determination of Creatinine in Hemodialysate, Analytical and Bioanalytical Chemistry, vol. 372, pp. 284-292, 2002.

(Continued)

*Primary Examiner* — Brian Szmal
*Assistant Examiner* — H. Q. Nguyen
(74) *Attorney, Agent, or Firm* — Rutan & Tucker, LLP

(57) ABSTRACT

A continuous Glomerular Filtration Rate (GFR) estimation system may include a Foley catheter, a continuous urine creatinine sensor, and a urine output monitor. The continuous GFR estimation system computes creatinine clearance as $CrCl=(U_{cr} \times U_{vol})/P_{cr} \times T_{min})$, where $U_{cr}$ is urine creatinine in mg/dL, $U_{vol}$ is urine volume in mL, $P_{cr}$ is plasma (serum) creatinine in mg/dL, and $T_{min}$ is time in minutes. A Foley catheter may be used to withdraw urine from the bladder. The urine may be delivered to a urine output monitor that provides the $U_{vol}$ value over a time $T_{min}$. Attached to the catheter is the flow-through continuous urine creatinine sensor for providing the $U_{cr}$ value. The remaining parameter is $P_{cr}$. Because serum creatinine levels do not change rapidly over time, a blood sample may be withdrawn prior to the start of the continuous GFR to obtain the $P_{cr}$ value.

23 Claims, 3 Drawing Sheets

(56) References Cited

U.S. PATENT DOCUMENTS

| | | | |
|---|---|---|---|
| 2006/0100743 A1* | 5/2006 | Townsend et al. | 700/266 |
| 2008/0119706 A1* | 5/2008 | Brister et al. | 600/365 |
| 2008/0243091 A1* | 10/2008 | Humphreys et al. | 604/264 |

FOREIGN PATENT DOCUMENTS

| | | | |
|---|---|---|---|
| JP | 2000513980 A | | 10/2000 |
| JP | 2002516722 A | | 6/2002 |
| WO | 9727481 A1 | | 7/1997 |
| WO | 9807029 A1 | | 2/1998 |
| WO | 2003043663 A1 | | 5/2003 |
| WO | 2006042093 A1 | | 4/2006 |
| WO | WO2007058461 | * | 5/2007 |
| WO | 2008103627 A2 | | 8/2008 |

OTHER PUBLICATIONS

Killiard et al., Creatinine biosensors: principles and designs, Trends in Biology, vol. 18, No. 10, pp. 433-437, Oct. 1, 2000.

Nguyen et al., Immobilized Enzyme Electrode for Creatinine Determination in Serum, Analytical Chemistry, vol. 63 pp. 611-614, 1991.

PCT/US2008/054207 filed Feb. 18, 2008 International Preliminary Report on Patentability dated Aug. 26, 2009.

PCT/US2008/054207 filed Feb. 18, 2008 Search Report dated Sep. 23, 2008.

PCT/US2008/054207 filed Feb. 18, 2008 Written Opinion dated Sep. 23, 2008.

Rowe et al. An Evaluation of Blood Creatinine Measurement by Creatinase on the NOVA M7 Blood Gas Analyzer, Clinica Chimica Acta, 2001, vol. 307, pp. 23-25, 2001.

Stefan-Van Staden et al., Simultaneous Detection of Creatine and Creatinine Using a Sequential Injection Analysis/Biosensor System, Prepative Biochemistry and Biotechnology, vol. 36, pp. 287-296, 2006.

JP 2009-550971 filed Feb. 18, 2008 First Office Action dated Apr. 18, 2012.

* cited by examiner

RENAL MONITOR

This application is a U.S. national stage application under 35 USC §371 of International Application No. PCT/US2008/054207, filed Feb. 18, 2008, claiming priority to U.S. Provisional Patent Application No. 60/890,851, filed Feb. 21, 2007, the disclosures of which is are incorporated herein by reference in their entirety.

Urine has been called the "canary of the body" and is an important vital sign because it often gives an early warning and gross indication of developing conditions within the body. Urine is produced from the kidneys, which filter toxins such as urea and creatinine (a waste product of protein metabolism) out of the blood. Because the body must produce urine to rid itself of toxins, the lack of urine signifies that the blood is not being purified, and that toxins are building up.

Renal (kidney) failure can be acute (quick onset due to injury or surgery) or chronic (e.g. failed kidneys requiting repeated dialysis). Kidney failure (renal dysfunction) caused by the low passage of blood through the kidneys (renal hypoperfusion) can dramatically increase death rates (mortality) in patients. Therefore, urine output monitoring is needed for patients recovering from surgery, critically ill patients, trauma patients and the like, many who come out of the Emergency Room (ER) or Operating Room (OR) and end up in an Intensive Care Unit (ICU), or patients with chronic renal failure.

Catheters and automated urine output monitoring devices have been developed to assist nursing staff in measuring the urine output for patients who have, or are candidates to have, either acute or chronic renal failure. However, urine is "downstream," both literally and figuratively, from the kidneys, and thus urine output alone is insufficient to determine whether the kidneys are performing properly. Thus, a need has been recognized for monitoring the kidneys for renal failure.

Each kidney includes filters known as glomeruli. The glomeruli are capillary blood vessels actively involved in the filtration of the blood. As with any filter, the glomeruli separate substances based upon their unique characteristics. The effectiveness of the glomeruli depends upon pressure, the selectivity characteristics of the membrane and its size or surface area. When the kidneys are optimal, the rate of filtration is high, but with renal dysfunction the ability to clear substances decreases. In particular, because a parameter referred to as the Glomerular Filtration Rate (GFR) is rapidly altered during renal hypoperfusion and serves as a measure of how well the kidneys are cleaning the blood, GFR measurements can allow for early detection of renal failure and prompt renal-specific therapy. Normal values for GFR are $120\pm30$ mls/min/1.73 m$^2$, while GFR values in the range of about 60 to 89 mls/min/1.73 m$^2$ are indicative of a slight decrease in kidney function, and GFR values less than 60 mls/min/1.73 m$^2$ suggest that some kidney damage may be present.

However, GFR cannot be measured directly. The urinary clearance of an ideal filtration market is considered the most accurate way to measure GFR, but this is cumbersome to implement in clinical practice. For example, one method for directly measuring renal function involves injecting an isotope into the patient's bloodstream. These markers (e.g. 5ICr-EDIA, 99Tc-DIPA) are cleared almost entirely by glomerular filtration (the filtering and removal of waste products by the kidneys), and therefore the measurement of their disappearance rate from the bloodstream and their appearance in the urine, can be used to compute the GFR. Thus, after the isotope is injected into the bloodstream, blood and urine samples are collected, and laboratory testing is performed to determine how much of the isotope is present in the patient's blood and urine. This entire process can take hours or days, during which time the function of the kidneys may have significantly changed, and provides only a single data point representative of kidney function.

Because the clearance of ideal filtration markers is impractical, serum levels of endogenous filtration markers (substances generated within the body) such as serum creatinine have traditionally been used to estimate GFR. Creatinine is a metabolite from muscle. Each day the muscles in the body go through "maintenance." As new muscle builds, old muscle cells are torn down and release this metabolite into the blood where it is eliminated by the kidneys and excreted into the urine. Therefore, a measurement of the ability of the kidneys to clear creatinine from the bloodstream (creatinine clearance) can be used to estimate the GFR. The creatinine clearance test compares the level of creatinine in urine with the creatinine level in the blood, usually based on measurements of a 24-hour urine sample and a blood sample drawn at the end of the 24-hour period.

Creatinine clearance approximates GFR but usually overestimates it due to the secretion of creatinine in the proximal tubule. Creatinine clearance (CrCl) over a 24-hour period can be estimated as CrCl (mls/min)=UV×1000×1000)/P×1440, where UV is the amount of creatinine in 24 hours of urine in mmol/24 h, P is serum creatinine in micromols/l, and 1440 is the number of minutes in 24 hours. In general, the timed creatinine clearance estimation equation can be represented as CrCl=$(U_{cr} \times U_{vol})/(P_{cr} \times T_{min})$, where $U_{cr}$ is urine creatinine in mg/dL, $U_{vol}$ is urine volume in mL, $P_{cr}$ is plasma (serum) creatinine in mg/dL, and $T_{min}$ is time in minutes.

Creatinine clearance can also be estimated from serum creatinine using estimating equations. For example, creatinine clearance can be estimated by the Cockroft-Gault equation CrCl=((140−age)×(weight)×123×(0.85 if female))/Creat, where Creat is serum creatinine in micromol/l. Some organizations recommend estimating GFR from serum creatinine using the Modification of Diet in Renal Disease (MDRD) Study equation. This equation uses serum creatinine in combination with age, sex and race to estimate GFR as GFR=$186 \times (P_{cr})^{-1.154} \times (age)^{-0.203} \times (0.742$ if female$) \times (1.210$ if black), where GFR is expressed in ml/min/1.73 m$^2$, $P_{Cr}$ is serum creatinine expressed in mg/dl, and age is expressed in years.

However, these GFR estimation equations become inaccurate in cases of extremes of age and body size, severe malnutrition or obesity, disease of skeletal muscle, paraplegia or quadriplegia, vegetarian diet, rapidly changing kidney function, prior to dosing drugs with significant toxicity that are excreted by the kidneys, or pregnancy. In such cases, although the timed (e. g. 24-hour) procedure is time consuming, such procedures may be required.

As the above creatinine clearance calculations demonstrate, the computation of creatinine clearance to approximate GFR may require a single serum creatinine reading or in some cases a timed collection of urine creatinine which is inconvenient and possibly inaccurate. Significantly, in any of the estimation methodologies, the GFR approximation methodologies provide only a single data point.

However, continuous monitoring of GFR is often needed to manage critically ill patients in an ICU setting for a host of conditions including, but not limited to, sepsis and kidney organ failure. Furthermore, knowledge of the GFR rate and the rate of change of GFR with respect to urine output, which can only be accurately obtained by continuous GFR monitoring, is often needed for therapeutic decision making and is not just a diagnostic test to indicate kidney function or lack thereof.

Applicants have recognized that it would be desirable to measure renal function and monitor for renal failure that is simpler, less invasive and continuous (provides real-time data) compared with present solutions.

BRIEF SUMMARY OF THE INVENTION

Accordingly, a non-invasive continuous Glomerular Filtration Rate (GFR) estimation system is described herein, the continuous GFR estimation system in one embodiment including a Foley catheter, a continuous urine creatinine sensor, a urine output monitor, and a creatinine clearance computational circuit. The continuous GFR estimation system measures creatinine clearance, which is a function of time, serum creatinine, urine output, and urine creatinine. As noted above, the timed creatinine clearance estimation equation can be represented as $CrCl=(U_{cr} \times U_{vol})/(P_{cr} \times T_{min})$, where $U_{cr}$ is urine creatinine in mg/dL, $U_{vol}$ is urine volume in mL, $P_{cr}$ is plasma (serum) creatinine in mg/dL, and $T_{min}$ is time in minutes.

A Foley catheter may be used to withdraw urine from the bladder. The urine itself may be delivered to a creatinine clearance measurement system, which includes a urine output monitor that measures total urine output, thus providing the $U_{vol}$ value of the creatinine clearance equation presented above. The urine output monitor provides the $U_{vol}$ value to a creatinine clearance computational circuit. Attached to the catheter is a flow-through creatinine sensor for continuous monitoring of urine creatinine, thus providing the $U_{Cr}$ value of the creatinine clearance equation presented above to the creatinine clearance computational circuit.

A continuous optical biosensor may be used for continuously detecting and measuring creatinine. The optical biosensor includes a sensor containing an analyte-specific chemical that interacts more specifically with one analyte than others, a light source and light detector. The sensor contains a chemical that interacts more specifically with creatinine than others analytes. Because the sensor forms a part of the catheter, as urine is drained from the body, the sensor is exposed to urine flow and changes one or more of its properties in a predictable manner depending on the amount of creatinine in the urine. The light source then shines through the changed sensor and causes a light interaction with the sensor. The light detector detects the light interaction, and sends a signal representative of the detected light interaction to a processor, state machine or other circuitry for analyzing the light interaction and determining the concentration of creatinine in the urine.

The remaining parameter in the creatinine clearance equation provided above is $P_{Cr}$, serum creatinine. Because serum creatinine levels do not change rapidly over time, a blood sample may be withdrawn from the patient prior to the start of the continuous GFR test and analyzed in a lab to obtain the serum creatinine value $P_{Cr}$. Because the serum creatinine value will be valid for eight or more hours, it does not have to be monitored on a continuous basis.

With all of the parameters for the calculation of creatinine clearance now provided, creatinine clearance can now be computed. An exemplary creatinine clearance computational circuit receives a urine creatinine signal from the continuous creatinine sensor and a total urine output signal from the urine output monitor. The digitized values for urine creatinine and total urine output may be transmitted to a processor along with an elapsed time signal. The creatinine clearance computational circuit may include a user interface for enabling a user to establish a start time so that total elapsed time can be determined, and for enabling the user to input a serum creatinine value obtained from a laboratory. Because all of the parameters except serum creatinine are received on a continuous basis, the creatinine clearance computational circuit is able to compute as estimate for creatinine clearance (and therefore GFR) on a continuous basis.

The creatinine clearance computational circuit may also include a continuous printing device or graphical display and memory for printing out and/or displaying and storing any one or more of the parameters being monitored and computed on a continuous basis to show the changes in creatinine levels in the urine, urine output and GFR, and the relationship between them, over time.

These and other embodiments, methods, features and advantages will become more apparent to those skilled in the art when taken with reference to the following more detailed description of the invention in conjunction with the accompanying drawings that are first briefly described.

DETAILED DESCRIPTION OF THE INVENTION

The following detailed description should be read with reference to the drawings. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Embodiments described herein relate generally to a non-invasive continuous GFR monitor for monitoring the kidneys. It should be noted that the continuous GFR monitor, as described herein, may be used for a number of different patient conditions, such as, but not limited to, sepsis and kidney organ failure, and can provide information needed for therapeutic decision-making. The continuous GFR monitor described herein is applicable to both acute and chronic renal failure.

Figure 1:
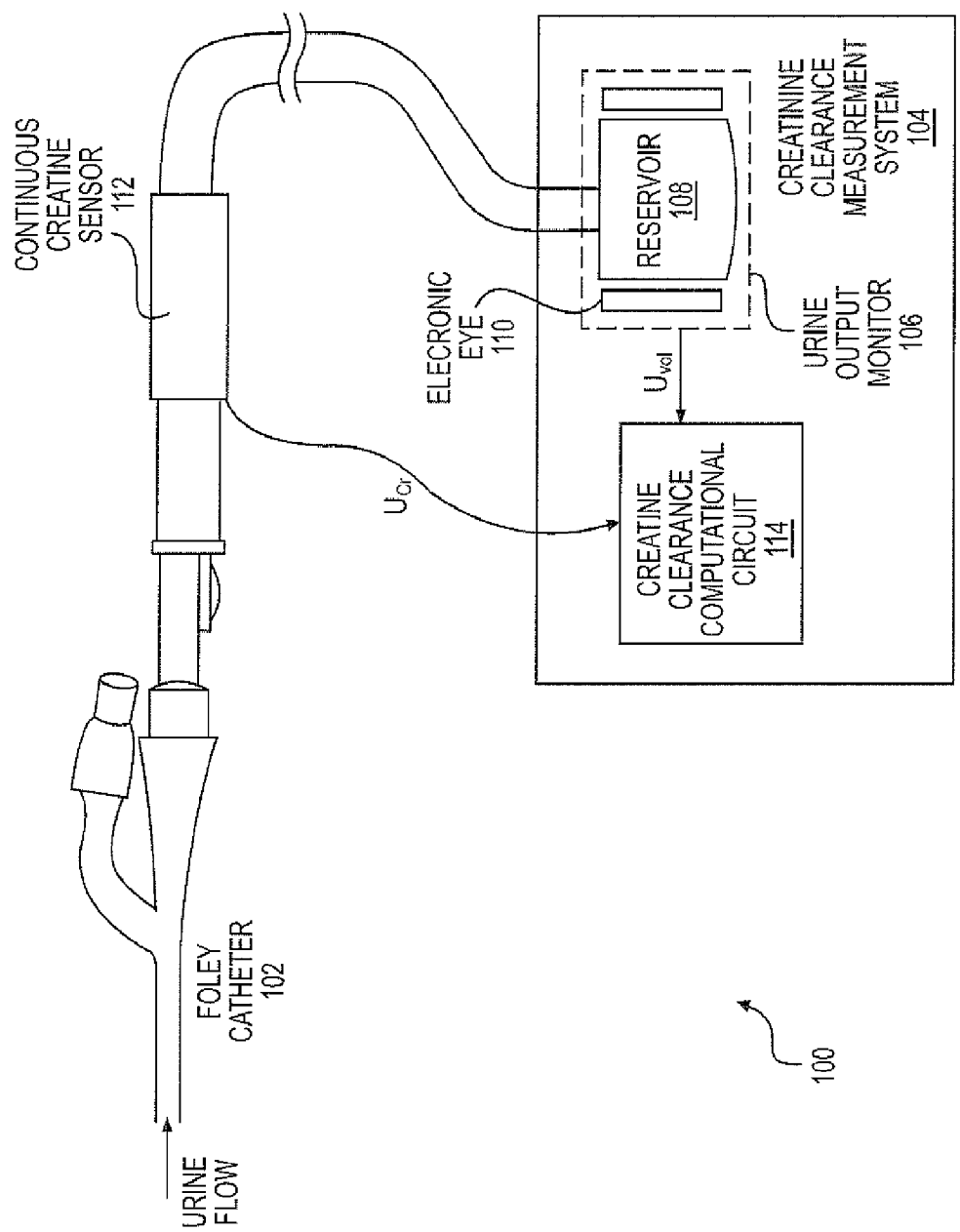
FIG. 1 is an illustration of an exemplary continuous GFR estimation system

FIG. 1 is an illustration of an exemplary continuous GFR estimation system 100 that measures creatinine clearance, although other elements can be monitored as well. Creatinine clearance is a function of time, serum creatinine, urine output, and urine creatinine. As noted above, the timed creatinine clearance estimation equation can be represented as $CrCl=(U_{cr} \times U_{vol})/(P_{cr} \times T_{min})$, where $U_{cr}$ is urine creatinine in mg/dL, $U_{vol}$ is urine volume in mL, $P_{cr}$ is plasma (serum) creatinine in mg/dL, and $T_{min}$ is time in minutes.

The GFR estimation system 100 may utilize a urine withdrawal device, such as a Foley catheter 102 (a flexible plastic tube inserted into the bladder to provide continuous urinary drainage) to withdraw urine from the bladder, although other methods of urine removal may be employed. The urine itself may be delivered to a creatinine clearance measurement system 104. The creatinine clearance measurement system 104 includes a urine output monitor 106 that measures total urine output, thus providing the $U_{vol}$ value of the creatinine clearance equation presented above. The urine output monitor 106 may include a reservoir 108 for urine and an electronic "eye" 110 that senses the urine level to determine total urine output on a real-time basis, either by continuously providing a total urine volume value $U_{vol}$ or by providing a total urine volume value $U_{vol}$ at periodic intervals. Either case is considered to be "continuous" monitoring as defined herein. An example urine output monitor is described in U.S. Pat. No. 4,343,316, which is incorporated by reference in its entirety into this application, and an example of a commercially available urine output monitor is the Bard CRITICORE Monitor, although any means of continuously measuring time and urine output may be employed. The urine output monitor 106 provides the $U_{vol}$ value to a creatinine clearance computational circuit 114.

Attached to the catheter is a flow-through continuous creatinine sensor 112 for continuous monitoring of urine creatinine, thus providing the $V_{Cr}$ value of the creatinine clearance equation presented above to the creatinine clearance computational circuit 114, either by continuously providing the urine creatinine concentration $V_{Cr}$ or by providing the urine creatinine concentration $V_{Cr}$ at periodic intervals. Either case is considered to be "continuous" monitoring as defined herein. The continuous creatinine sensor 112 may be one of the creatinine sensors known in the art. Creatinine sensors may be biosensors including a chemical recognition component that reacts to creatinine and a transducer component that detects and measures the reaction. The chemical recognition component may be biocatalytic (i.e., an enzyme) and the transducer may be electrochemical (e.g., amperometiic, voltametric) or optical (e.g., absorbance or fluorescence measurement). Examples of biosensors constructed using these technologies are described in "Creatinine biosensors: principles and designs" by A. J. Killiard and M. R. Smyth, Trends in Biotechnology, Volume 18, Number 10, Oct. 1, 2000, pp. 433-37 (hereinafter "Killiard"), which is incorporated by reference in its entirety into this application.

In general, optical creatinine sensors shine light into the urine stream. The sensor then measures the light received back from the urine stream, accounting for reflection, refraction, and absorption. Based on the principles of spectroscopy, the received light provides an indication of the content of the urine.

Figure 2A:
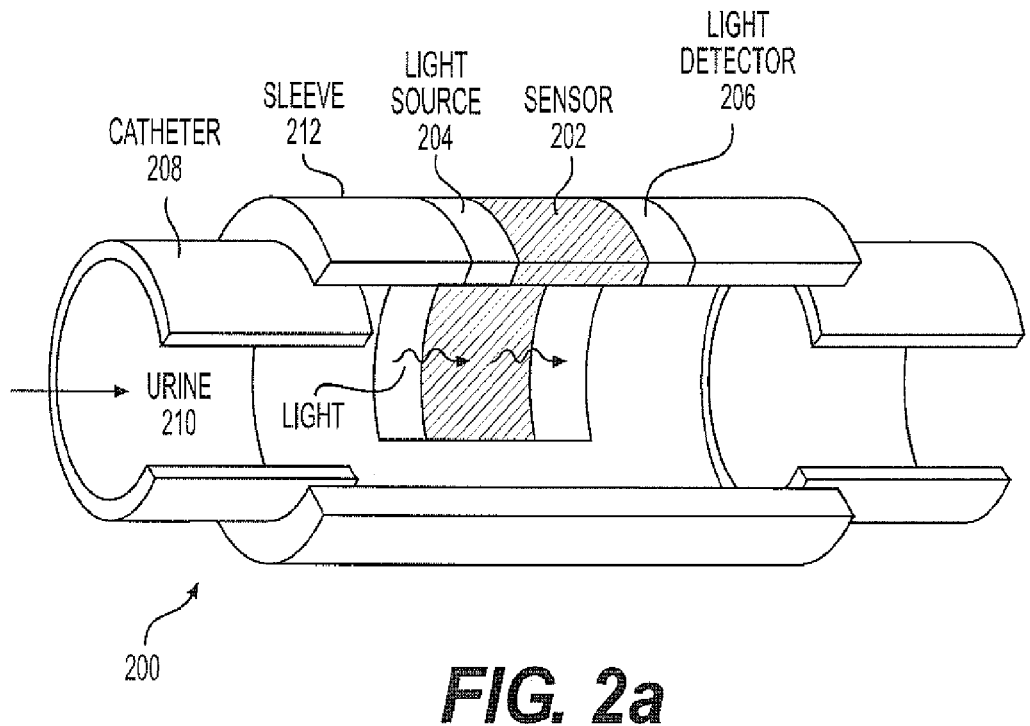
FIG. 2a is an illustration of an exemplary continuous optical biosensor that may be used for continuously detecting and measuring creatinine.

FIG. 2a is an illustration of a continuous optical biosensor 200 that may be used for continuously detecting and measuring creatinine. It should be emphasized that the configuration shown in FIG. 2a is merely exemplary, and that other configurations employing the same basic principles fall within the scope of the invention. The optical biosensor 200 of FIG. 2a is a sleeve 212 into which a catheter may be inserted at both ends. Incorporated into the walls of the sleeve 212 is a sensor 202 containing an analyte-specific chemical that interacts, more specifically with one analyte than others, a light source 204 and light detector 206. The sensor 202 contains a chemical that interacts more specifically with creatinine than other analytes. Because the sensor 202 forms a part of catheter 208, as urine 210 is drained from the body, the sensor is exposed to urine flow and changes one or more of its properties in a predictable manner depending on the amount of creatinine in the urine. The light source 204 then shines through the changed sensor 202 and causes a light interaction with the sensor. The light detector 206 detects the light interaction, and sends a signal representative of the detected light interaction to a processor, state machine or other circuitry for analyzing the light interaction and determining the concentration of creatinine in the urine. The general principles of the optical biosensor 200 are generally disclosed in U.S. Pat. No. 6,379,969 by Ganapati R. Mauze et al. (hereinafter "Mauze"), which is incorporated by reference in its entirety into this application. Although Mauze is not specifically directed to the flow-through detection and measurement of creatinine, U.S. Pat. No. 5,704,353 by Irvin Kalb (hereinafter "Kalb"), which is incorporated by reference in its entirety into this application, discloses optical sensors incorporated into a catheter for flow-through monitoring.

Figure 2B:
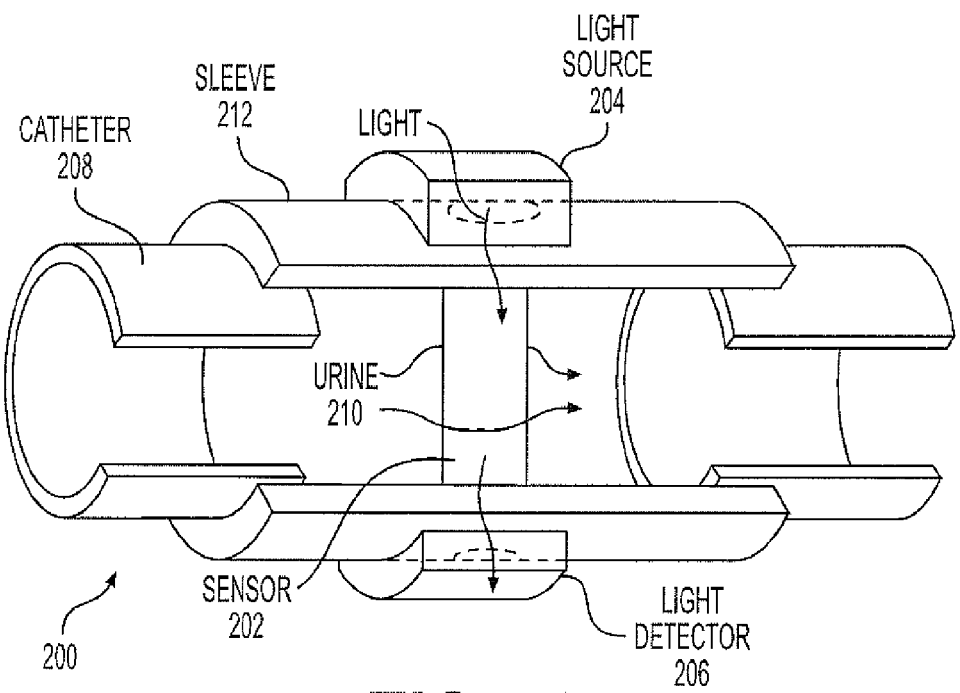
FIG. 2b is an illustration of another exemplary continuous optical biosensor that may be used for continuously detecting and measuring creatinine.

An alternative optical sensor design is illustrated in FIG. 2b. In FIG. 2b, disposed across the interior of sleeve 212 is a sensor 202 containing an analyte-specific chemical that interacts more specifically with one analyte than others. The sensor 202 is positioned to maximize its contact with urine 210 flowing through the sleeve 212. A light source 204 shines a light through the sensor 202 and causes a light interaction with the sensor. A light detector 206 positioned on the opposite side of the sleeve 212 detects the light interaction, and sends a signal representative of the detected light interaction to a processor, state machine or other circuitry for analyzing the light interaction and determining the concentration of creatinine in the urine.

Another type of sensor is a Clark electrode, which is an electrode coated with a compound that changes upon interaction with the creatinine molecules, providing a voltage gradient that can be used to measure creatinine levels. Clark electrode creatinine sensors are discussed in "Immobilized Enzyme Electrode for Creatinine Determination in Serum" by Vu Khue Nguyen et al., Analytical Chemistry, Volume 63 pp. 611-14 (hereinafter "Nguyen"), which is incorporated by reference in its entirety into this application. Although Nguyen discloses a Clark electrode for detecting creatinine in serum, the concepts are generally applicable to urine as well. Yet another type of sensor is an optrode, which is a combination of an optical and a Clark electrode.

A continuous enzymatic biosensor may also be used for continuously detecting and measuring creatinine according to embodiments described herein. The principles of the enzymatic biosensor are disclosed in an article entitled "Biosensors and flow-through system for the determination of creatinine in hemodialysate," by Ansgar Erlenkotter et al in the Analytical and Bioanalytical Chemistry Journal, January 2002, Vol. 372, pp. 284-92 (hereinafter "Erlenkotter"), which is incorporated by reference in its entirety into this application. Although the biosensor of Erlenkotter is discussed with respect to hemodialysate, the same principles are generally applicable to urine. Fundamentally, the sensor includes a platinum working electrode, a silver/silver chloride reference electrode and a carbon counter electrode. A multi-enzyme sequence of creatininase (CA), creatinase (CI) and sarcosine oxidase (SO) is applied to the working electrode, with a semipermeable membrane of a polymer such as Nafion formed between the working electrode and the enzyme layer to exclude interfering substances from the working electrode. When the working electrode comes into contact with the hemodialysate (or urine), amperometrically (i.e., based on electric current) detectable amounts of hydrogen peroxide are produced.

The remaining parameter in the creatinine clearance equation provided above is $P_{Cr}$, serum creatinine. Embodiments described herein take advantage of the fact that serum creatinine levels do not change rapidly over time. Therefore, a blood sample may be withdrawn from the patient prior to the start of the continuous GFR test and analyzed in a lab to obtain the serum creatinine value $P_{Cr}$. Because the serum creatinine value will be valid for eight or more hours, it does not have to be monitored on a continuous basis.

With all of the parameters for the calculation of creatinine clearance now provided, creatinine clearance can be computed. The values may be provided to a processor, state machine, or other circuitry as understood by those skilled in the art to compute creatinine clearance, with analog-to-digital (A/D) converters utilized where necessary.

Figure 3:
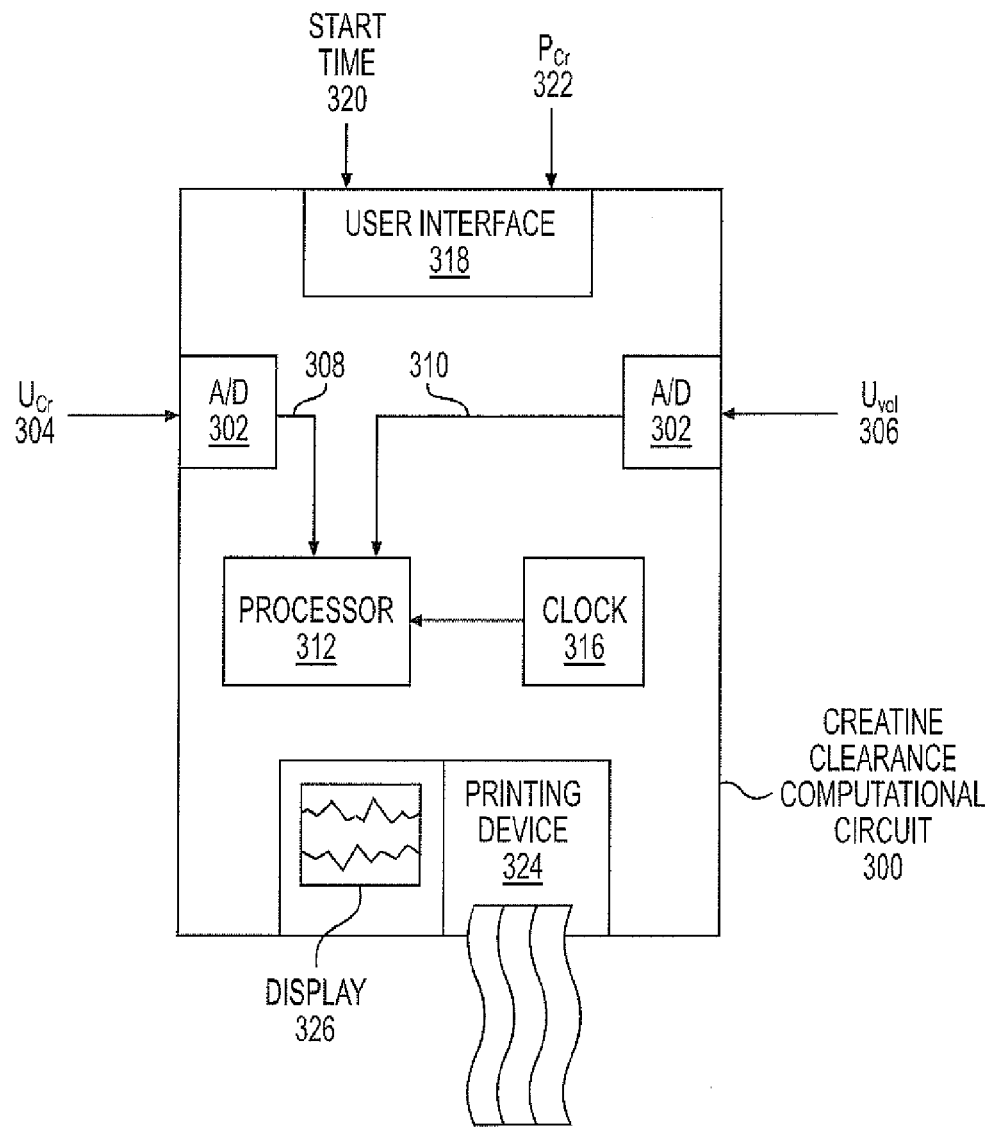
FIG. 3 is an illustration of an exemplary creatinine clearance computational circuit.

FIG. 3 is an illustration of an exemplary creatinine clearance computational circuit 300 which may include A/D converters 302 for receiving a urine creatinine signal 304 from a continuous creatinine sensor and a total urine output signal 306, if those signals are in analog form. The digitized values for urine creatinine 308 and total urine output 310 may be transmitted to a processor 312 along with an elapsed time signal 314 from a clock circuit 316. The creatinine clearance computational circuit 300 may include a user interface 318 for enabling a user to establish a start time 320 so that total elapsed time 314 can be determined, and for enabling the user to input a serum creatinine value 322 obtained from a laboratory. Because all of the parameters except serum creatinine are received 322 on a continuous basis, the creatinine clearance computational circuit 300 is able to compute as estimate for creatinine clearance (and therefore GFR) on a continuous basis.

The creatinine clearance computational circuit 300 may also include a continuous printing device 324 or graphical display 326 and memory for printing out and/or displaying and storing any one or more of the parameters being monitored and computed on a continuous basis to show the changes in creatinine levels in the urine, urine output and GFR, and the relationship between them, over time. The display or printout may provide continuous (connected) graphs of the parameters, or may provide data points at periodic intervals. Either case is considered to be "continuous" displaying or printing as defined herein.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein

What is claimed is:

1. A continuous Glomerular Filtration Rate (GFR) estimation system, comprising:
    a continuous creatinine sensor disposed on a catheter and configured to provide a continuous indication of creatinine concentration in urine as the urine flows through the catheter;
    a urine output monitor configured to provide an indication of total urine output; and
    a creatinine clearance computational circuit coupled to the continuous creatinine sensor and the urine output monitor and configured to receive the indication of creatinine concentration in the urine, the total urine output, a serum creatinine level and an elapsed time measurement, and continuously compute a creatinine clearance value representative of the GFR, such that multiple data points for the creatinine clearance value representative of the GFR are obtained during a single urine collection.

2. The continuous GFR estimation system according to claim 1, the creatinine clearance computational circuit comprising a user interface configured to enable a user to input a serum creatinine level.

3. The continuous GFR estimation system according to claim 1, the creatinine clearance computational circuit comprising a display device configured to display one or more of the estimated GFR, the total urine output, and the creatinine concentration.

4. The continuous GFR estimation system according to claim 1, wherein the catheter is at least partially positioned in a bladder of a patient to drain the urine from the bladder, the continuous creatinine sensor configured to sense the creatinine concentration in the urine being drained through the catheter, and the urine output monitor coupled to the catheter and configured to receive the urine being drained through the catheter.

5. The continuous GFR estimation system according to claim 1, the continuous creatinine sensor comprising an optical sensor.

6. The continuous GFR estimation system according to claim 5, the optical sensor comprising a biosensor reactive to creatinine, a light source for shining light through the biosensor after the biosensor has been exposed to the creatinine, and a light detector for detecting the light being received through the biosensor.

7. The continuous GFR estimation system according to claim 6, the biosensor formed within the continuous creatinine sensor and configured to be exposed to urine flow.

8. The continuous GFR estimation system according to claim 1, the creatinine clearance computational circuit comprising a processor configured to receive the indication of creatinine concentration in the urine, the total urine output, the serum creatinine level and the elapsed time measurement, and compute a creatinine clearance value representative of the GFR.

9. The continuous GFR estimation system according to claim 1, wherein the creatinine clearance computational circuit is further configured to estimate a rate of change of GFR.

10. The continuous GFR estimation system according to claim 1, further comprising a continuous graphical display and memory configured to display and store monitored values of creatinine concentration in the urine, total urine output, the creatinine clearance value representative of GFR, and the relationship between them over time.

11. The continuous GFR estimation system according to claim 5, wherein a wall of the optical sensor comprises:
    a sensor portion containing an analyte-specific chemical that interacts more specifically with creatinine than other analytes;
    a light source adjacent a first side of the sensor portion; and
    a light detector adjacent a second side of the sensor portion, wherein the light source shines light through the sensor portion to the light detector in a direction parallel to urine flow.

12. The continuous GFR estimation system according to claim 5, the optical sensor further comprising a sensor portion containing an analyte-specific chemical that interacts more specifically with creatinine than other analytes is disposed across an interior of the optical sensor in a position that maximizes contact between the sensor portion and the urine flowing through the optical sensor, and a light source on a first side of the optical sensor that shines light through the sensor portion to a light detector on an opposite side of the optical sensor.

13. A method for continuously estimating Glomerular Filtration Rate (GFR), comprising:
continuously determining a creatinine concentration in urine being drained using a continuous creatinine sensor disposed on a portion of a catheter, the continuous creatinine sensor providing a continuous indication of creatinine concentration in urine while urine flows through the catheter;
continuously determining a total output of the urine being drained; and
continuously computing a creatinine clearance value representative of the GFR on a creatinine clearance computational circuit, based on the continuously determined creatinine concentration in the urine, the continuously determined total output of the urine, a serum creatinine level and an elapsed time measurement, such that multiple data points for the creatinine clearance value representative of the GFR are obtained during a single urine collection.

14. The method according to claim 13, further comprising generating the serum creatinine level by taking a blood sample and testing the sample for serum creatinine prior to a start of continuously computing the creatinine clearance value.

15. The method according to claim 13, further comprising continuously displaying and continuously updating one or more of the estimated GFR, the total urine output, and the creatinine concentration.

16. The method according to claim 13, wherein the continuous creatinine sensor comprises an optical sensor, and wherein continuously determining the creatinine concentration in the urine being drained comprises using the optical sensor.

17. The method according to claim 16, further comprising sensing the creatinine concentration in the urine being drained by exposing a creatinine-reactive biosensor to the creatinine, shining light through the biosensor, and detecting the light being received through the biosensor.

18. The method according to claim 17, further comprising placing the biosensor within a flow of the urine being drained.

19. The method according to claim 13, further comprising sensing the creatinine concentration in the urine being drained using a Clark electrode.

20. The method according to claim 13, further comprising sensing the creatinine concentration in the urine being drained using an enzymatic sensor.

21. The method according to claim 13, further comprising computing a rate of change of the creatinine clearance value representative of the GFR on the creatinine clearance computational circuit.

22. The method according to claim 16, wherein the optical sensor comprises a sensor portion containing an analyte-specific chemical that interacts more specifically with creatinine than other analytes, a light source adjacent a first side of the sensor portion, and a light detector adjacent a second side of the sensor portion, wherein continuously determining the creatinine concentration in the urine being drained further comprises:
exposing the sensor portion to the urine as the urine flows through the catheter;
shining light through the sensor portion in a direction parallel to urine flow; and
detecting the light passing through the sensor portion.

23. A method for providing a continuous estimate of Glomerular Filtration Rate (GFR), comprising:
continuously computing a creatinine clearance equation $CrCl=(U_{Cr} \times U_{vol})/(P_{Cr} \times T_{min})$, where $U_{Cr}$ is urine creatinine in mg/dL, $U_{vol}$ is urine volume in mL, $P_{Cr}$ is serum creatinine in mg/dL, and $T_{min}$ is time in minutes, such that multiple data points for creatinine clearance are obtained during a single urine collection;
wherein the $U_{Cr}$ value is determined by continuously sensing and monitoring a creatinine concentration in urine being drained using a continuous creatinine sensor disposed on a portion of a catheter, the continuous creatinine sensor providing a continuous indication of creatinine concentration in urine while urine flows through the catheter;
wherein $U_{vol}$ value is determined on a creatinine clearance computational circuit by continuously measuring a total output of the urine being drained;
wherein $T_{min}$ is an elapsed test time tracked throughout the providing of the continuous estimate of GFR; and
wherein the $P_{Cr}$ value is obtained from a blood sample prior to a start of the providing of the continuous estimate of GFR, and assumed to be constant throughout the providing of the continuous estimate of GFR.

\* \* \* \* \*